(12) United States Patent
Yi et al.

(10) Patent No.: US 8,015,712 B2
(45) Date of Patent: Sep. 13, 2011

(54) SAFETY SCALPEL

(75) Inventors: Patrick Yi, Singapore (SG); Hong-Minh Le, Singapore (SG)

(73) Assignee: Medipurpose Pte Ltd (SG)

( * ) Notice: Subject to any disclaimer, the term of this patent is extended or adjusted under 35 U.S.C. 154(b) by 849 days.

(21) Appl. No.: 11/613,065

(22) Filed: Dec. 19, 2006

(65) Prior Publication Data
US 2007/0265651 A1    Nov. 15, 2007

Related U.S. Application Data (63) Continuation-in-part of application No. 11/259,939, filed on Oct. 26, 2005, now Pat. No. 7,669,337.

(60) Provisional application No. 60/623,741, filed on Oct. 29, 2004.

(51) Int. Cl.
  *A61B 17/32*   (2006.01)
(52) U.S. Cl. .......................................... 30/162; 606/167
(58) Field of Classification Search ................. 606/167, 606/170; 30/162, 163, 335, 336, 2, 339
See application file for complete search history.

(56) References Cited

U.S. PATENT DOCUMENTS

| | | | |
|---|---|---|---|
| 5,299,357 A | 4/1994 | Wonderley et al. | |
| 5,330,493 A * | 7/1994 | Haining | 606/167 |
| 5,342,379 A | 8/1994 | Volinsky | |
| 5,741,289 A | 4/1998 | Jolly et al. | |
| 5,868,771 A | 2/1999 | Herbert et al. | |
| 5,924,206 A | 7/1999 | Cote et al. | |
| 5,941,892 A * | 8/1999 | Cohn et al. | 606/167 |
| 6,022,364 A | 2/2000 | Flumene et al. | |
| 6,053,929 A | 4/2000 | Cohn et al. | |
| 6,254,621 B1 | 7/2001 | Shackelford et al. | |
| 6,589,258 B2 | 7/2003 | Pilo et al. | |
| 6,757,977 B2 | 7/2004 | Dambal et al. | |
| 6,884,240 B1 | 4/2005 | Dykes | |
| 7,172,611 B2 | 2/2007 | Harding et al. | |
| 7,207,999 B2 * | 4/2007 | Griffin et al. | 606/167 |
| 7,669,337 B2 | 3/2010 | Yi et al. | |
| 2006/0095057 A1 | 5/2006 | Yi et al. | |

FOREIGN PATENT DOCUMENTS

| | | |
|---|---|---|
| EP | 0 958 788 A1 | 11/1999 |
| EP | 1 031 322 A2 | 8/2000 |
| JP | 6021745 | 2/1985 |
| JP | 63172411 | 11/1998 |
| JP | 11318914 | 11/1999 |

(Continued)

OTHER PUBLICATIONS

U.S. Appl. No. 60/623,741 for Patrick Yi, et al. entitled "Safety Scalpel", filed Oct. 29, 2004.

(Continued)

*Primary Examiner* — Kenneth E. Peterson
(74) *Attorney, Agent, or Firm* — Ryan A. Schneider, Esq.; Jihan A. R. Jenkins, Esq.; Troutman Sanders LLP (57) ABSTRACT

A safety scalpel that incorporates a reusable metal scalpel handle similar in shape and feel to the conventional metal handle preferred by most surgeons, and a disposable blade cartridge that covers the blade before, during and after use, and is easily mounted and released from the scalpel handle. The blade cartridge includes a blade with similar cutting profiles as standard surgical blades, a blade holder that is permanently fixed to the blade, and a blade guard that covers the blade and within which the blade holder is able to slide. The scalpel handle is reusable, while the blade cartridge is disposable. The blade cartridge is attachable and detachable from the scalpel handle.

14 Claims, 12 Drawing Sheets

FOREIGN PATENT DOCUMENTS

| | | |
|---|---|---|
| JP | 2003339723 | 12/2003 |
| WO | 2008077084 A1 | 6/2008 |

OTHER PUBLICATIONS

The Notification of the First Office Action dated Jun. 7, 2010 issued by the State Intellectual Property Office of P.R. China for related Chinese Application No. 200780045244.X.

International Search Report dated Mar. 3, 2006 for Related Application No. PCT/US2005/038588.

International Search Report and Written Opinion dated May 13, 2008 for Related Application No. PCT/US2007/088054.

Preliminary Notice of Rejection dated Dec. 21, 2010 for related Japanese Application No. 2007-539071.

* cited by examiner

SAFETY SCALPEL

CROSS REFERENCE TO RELATED APPLICATION AND CLAIM OF BENEFIT

This application is a continuation-in-part application of U.S. patent application Ser. No. 11/259,939, filed on Oct. 26, 2005, now U.S. Pat. No. 7,669,337, which claims priority to U.S. Provisional Patent Application No. 60/623,741, filed on 29 Oct. 2004.

FIELD OF THE INVENTION

The present invention relates generally to scalpel devices and, in particular, to safety scalpels for medical use.

BACKGROUND OF THE INVENTION

Health care is the second fastest growing sector of the U.S. economy, employing over 12 million workers. Health care workers face a wide range of hazards on the job, including needlestick and sharps injuries, back injuries, latex allergies, violence, and stress. Although it is possible to prevent or reduce health care worker exposure to these hazards, health care workers are actually experiencing increasing numbers of occupational injuries and illnesses. Rates of occupational injury to health care workers have risen over the past decade. By contrast, two of the most hazardous industries, agriculture and construction, are safer today than they were a decade ago.

Precise national data is not available on the annual number of needlestick and other percutaneous injuries among health care workers; however, estimates indicate that 600,000 to 800,000 such injuries occur annually. About half of these injuries go unreported. Data from EPINet (the Exposure Prevention Information Network) suggests that at an average hospital, workers incur approximately thirty needlestick injuries per 100 beds per year.

Most reported needlestick and sharps injuries involve nursing staff; but laboratory staff, physicians, housekeepers, and other health care workers are also injured. Some of these injuries expose workers to bloodborne pathogens that can cause infection. The more serious of these pathogens are the hepatitis B virus (HBV), the hepatitis C virus (HCV), and the human immunodeficiency virus (HIV). Infections by each of these pathogens are potentially life threatening, yet preventable.

The emotional impact of needlestick and sharps injuries can be severe and long lasting, even when a serious infection is not transmitted. This impact is particularly severe when the injury involves exposure to HIV. In one study of twenty health care workers with an HIV exposure, eleven reported acute severe distress, seven had persistent moderate distress, and six quit their jobs as a result of the exposure. Other stress reactions requiring counseling have also been reported. Not knowing the infection status of the source patient can accentuate the health care worker's stress. In addition to the exposed health care worker, colleagues and family members may suffer emotionally.

Safety and health issues can best be addressed in the setting of a comprehensive prevention program that considers all aspects of the work environment and that has employee involvement as well as management commitment. Implementing the use of improved engineering controls is one component of such a comprehensive program. Other prevention strategy factors that must be addressed, however, include modification of hazardous work practices, administrative changes to address needle hazards in the environment (e.g., prompt removal of filled sharps disposal boxes), safety education and awareness, feedback on safety improvements, and action taken on continuing problems.

Improved engineering controls are often among the most effective approaches to reducing occupational hazards and, therefore, are an important element of a needlestick prevention program. Such controls include eliminating the unnecessary use of needles and implementing devices having safety features. A number of sources have identified several desirable characteristics for safety devices, which include preferences for safety devices that: do not use needles; incorporate the safety feature as an integral part of the device; work passively (i.e., requires no activation by the user); have a safety feature that can be engaged with a single-hand technique and allows the worker's hands to remain behind the exposed sharp, if user activation is necessary; allow the user to easily determine whether the safety feature is activated; have a safety feature that cannot be deactivated and remains protective through disposal; perform reliably; are easy to use and practical; and are safe and effective for patient care.

Although each of these characteristics is desirable, some are not feasible, applicable, or available for certain health care situations. For example, needles will always be necessary where alternatives for skin penetration are not available. Also, a safety feature that requires activation by the user might be preferable to one that is passive in some cases. Each device must be considered on its own merit and ultimately on its ability to reduce workplace injuries.

Regarding specifically scalpels, the conventional scalpel currently used in the healthcare industry includes a metal handle and a disposable blade that is mounted on the handle prior to use, and removed after use. The process of mounting and dismounting of the blade is a difficult and dangerous procedure, which exposes the medical practitioner to potential injury from the exposed blade and contamination due to blood that may be present on the blade. Further, sharps injuries may also occur during an operation as the surgeon passes the exposed scalpel to a colleague.

Surgeons who have developed a feel for the shape and weight of the metal handle dislike the current disposable safety scalpels as, among other things, the plastic handle is too light and feels "different." During use, the plastic handle of the scalpel incurs undesirable flexibility than that of a metal handle scalpel. In addition, the disposable safety scalpel is significantly more expensive than the regular disposable blade. These two factors currently limit the adoption of safety scalpels in the healthcare industry.

What is needed is a safe and reliable scalpel that overcomes the present objections from the healthcare practitioner of current designs, while providing adequate protection for the medical workers handling the scalpel. It is to such a device that the present invention is primarily directed.

SUMMARY OF THE INVENTION

Briefly described, in a preferred form, the present invention is an improvement over the conventional scalpel by providing a safety scalpel that incorporates a reusable metal scalpel handle similar in shape and feel to the conventional metal handle preferred by most surgeons, and a disposable blade cartridge that covers the blade before, during, and after use, and is easily mounted and released from the metal scalpel handle.

The present safety scalpel comprises a blade with similar cutting profiles as standard surgical blades, a blade holder that is fixed to the blade, a blade guard that covers the blade and within which the blade holder is able to slide, a scalpel handle that receives a blade cartridge (being the blade, blade holder and blade guard assembled together), and a locking assembly. The scalpel handle is reusable, while the blade cartridge is disposable.

While prior art designs have incorporated disposable blade cartridges where the blade guard slides off the releaseably fixed blade, the present invention is based on the blade sliding out of the releaseably fixed guard.

The present invention comprises a safety disposable blade cartridge that can be used with either a preferably reusable metal, or disposable plastic, scalpel handle, having the weight and feel of conventional designs. The blade cartridge easily fixes onto the scalpel handle, and yet is securely and releasably locked on the scalpel handle. The blade is preferably movable through at least three distinct positions—open, closed, and locked.

Attaching and detaching the blade cartridge to the scalpel handle utilizes an easy, longitudinal sliding motion. When fixed to the scalpel handle, only the blade and blade holder of the blade cartridge can move in a longitudinal direction, as the blade guard experiences limited or no longitudinal movement.

In other preferred embodiments, the blade cartridge is itself a standalone mini-scalpel, which is securely fixed to a passive metal handle or the blade can move within a hollow metal holder.

DETAILED DESCRIPTION

Referring now in detail to the figures, wherein like reference numerals represent like parts throughout the several views, the present safety scalpel 10 of FIGS. 1A, 1B, and 6A-6C, comprises a blade 100 is fixable to a blade holder 200, which subassembly is slideable within a blade guard 300. The combination of the blade 100, the blade holder 200, and the blade guard 300 forms a blade cartridge 400, attachable to a scalpel handle 500.

The present safety scalpel 10 comprises the blade cartridge 400 and the scalpel handle 500, such that the blade cartridge 400 is configured for secure attachment to and safe detachment from the scalpel handle 500. In a preferred embodiment of the present invention, the blade cartridge 400 is disposable, while the scalpel handle 500 is non-disposable. Accordingly, a new blade cartridge 400 can be attached to the scalpel handle 500 for use by, for example, a medical practitioner. After the medical practitioner has finished using the safety scalpel 10, the blade cartridge 400 can be safely removed from the scalpel handle 500, so that the blade cartridge 400 can be disposed of properly.

The blade cartridge 400 can comprise the blade 100, the blade holder 200 adapted to securely engage the blade 100, and the blade guard 300 configured to slideably receive the blade 100 and blade holder 200. Further, the blade holder 200 is adapted to move the blade 100, or a portion thereof, between a closed and open position. In the closed position, the blade 100 is safely and fully contained within the blade guard 300. In the open position, the blade 100, or a portion thereof, extends beyond the blade guard 300. As designed, the blade 100 is in the closed position during non-use of the safety scalpel 10 and in the open position during active use of the safety scalpel 10. The safety scalpel 10 of the present invention, therefore, provides a safe and effective surgical tool.

Figure 2A:
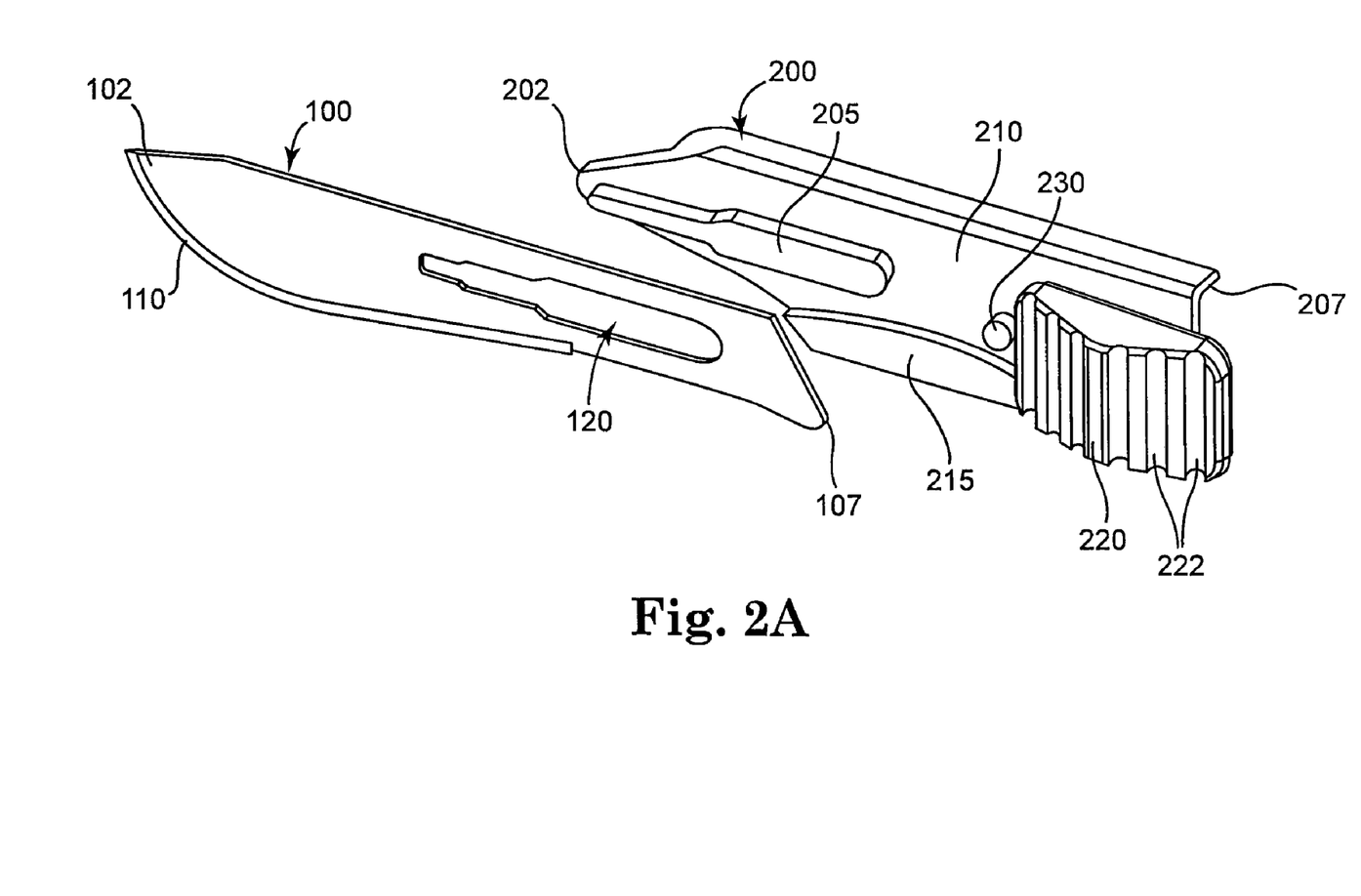
FIG. 2A illustrates a perspective view of an unassembled blade and a blade holder in accordance with a preferred embodiment of the present invention.
Figure 2B:
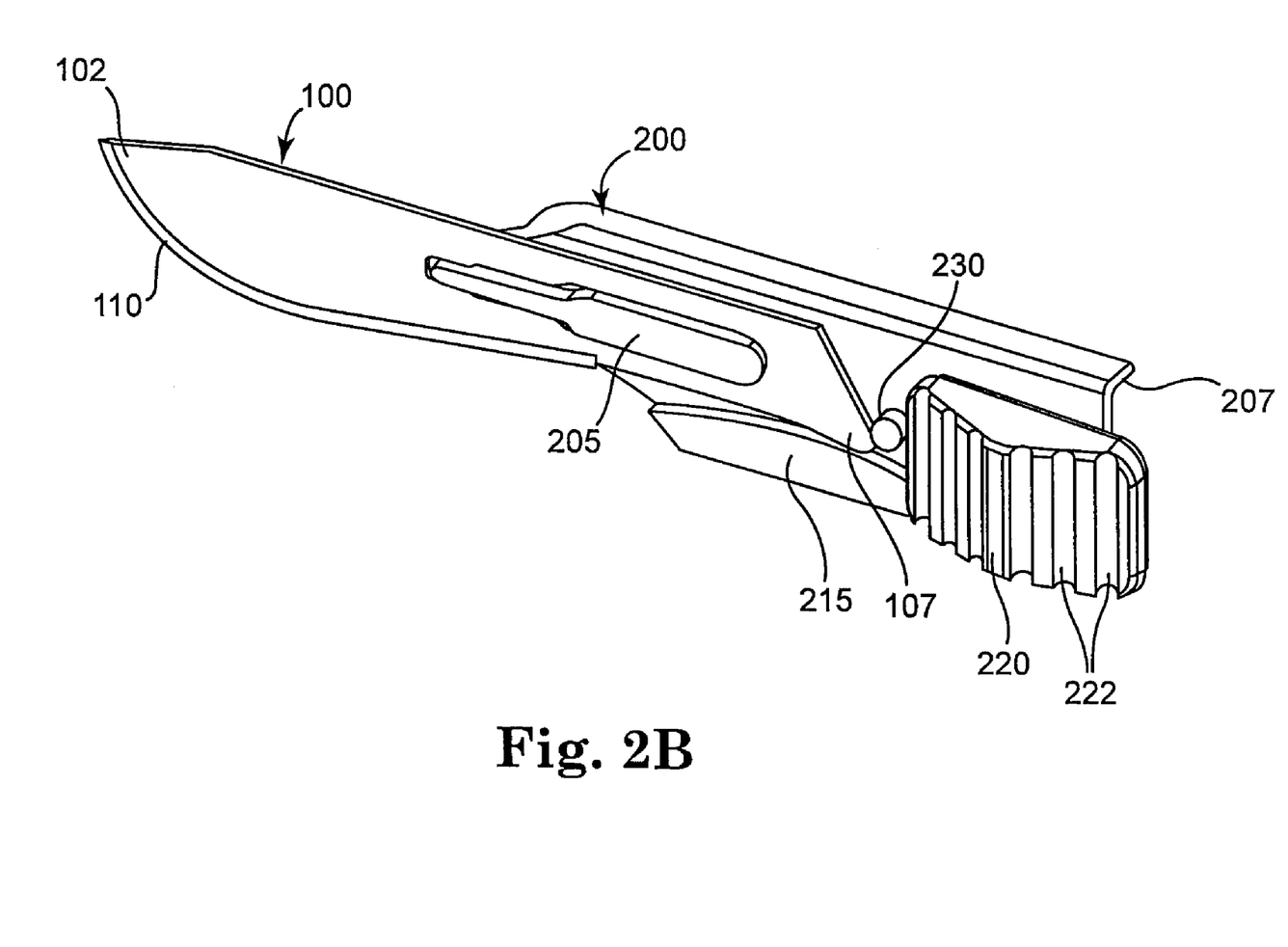
FIG. 2B illustrates a perspective view of the assembled blade and blade holder of FIG. 2A.

As illustrated in FIGS. 2A and 2B, the blade 100 includes a cutting edge 110 located at a distal end 102 of the blade 100. Further, at a proximal end 107, the blade 100 defines an aperture 120; preferably an elongated aperture 120 such as a slot. Other than perhaps the profile of the cutting edge 110, the blade 100 preferably has a similar front and back face.

One skilled in the art will recognize that the blade 100 can be made of a variety of suitable materials including, but not limited to, both carbon and stainless steel. Generally, the carbon and stainless steel used to create the blade 100 are manufactured in compliance with several industry standards including British Standard ("BS") 2982:1992, International Organization for Standardization ("ISO") 7740:1985 and European Standard ("EN") 27740:1992. The blade 100 further can be sterilized by, for example, gamma radiation.

Figure 2C:
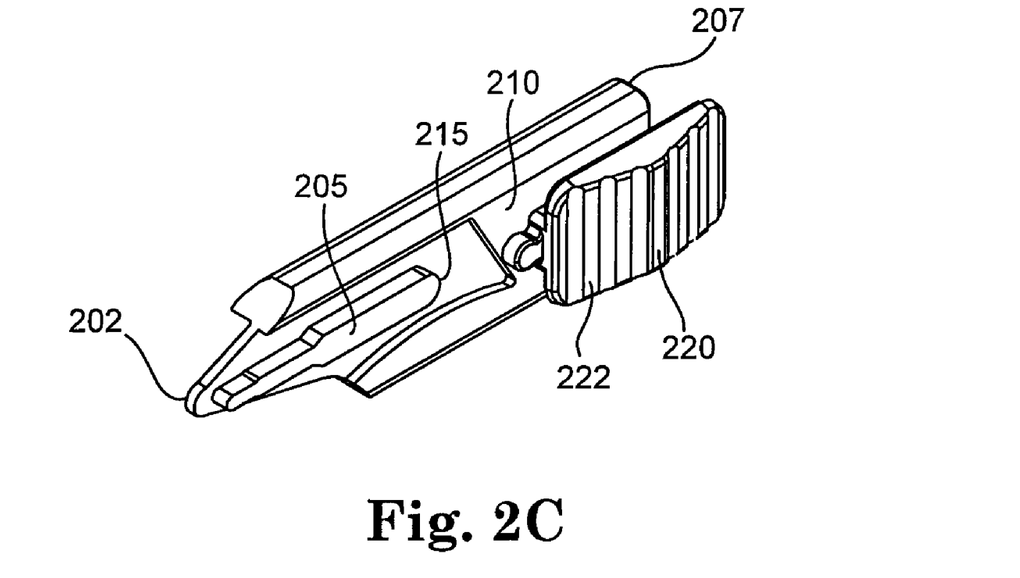
FIG. 2C illustrates a perspective view of a front face of a blade holder in accordance with preferred embodiment of the present invention.
Figure 2D:
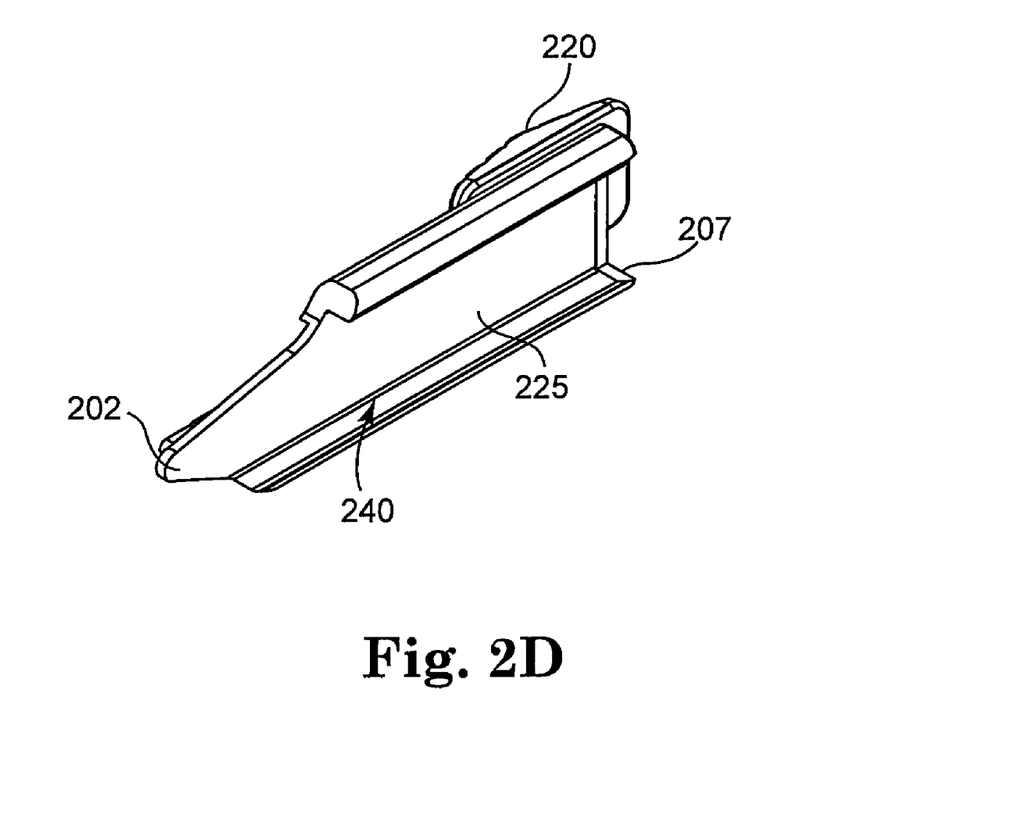
FIG. 2D illustrates a perspective view of a back face of the blade holder of FIG. 2C.

The blade holder 200 is designed to mate with blade 100. Unlike the blade 100, the front face 210 and back/rear face 225 of the blade holder 200 are dissimilar, and the thickness of the blade holder 200 is non-uniform. A distal end 202 of blade holder 200 comprises a holder protrusion 205 extending from the front face 210 of the blade holder 200, in a profile that generally corresponds to the aperture 120 of the blade 100. The holder protrusion 205 is adapted to be securely engaged in the aperture 120 of the blade 100.

The blade holder 200 can further comprise a protrusion notch 215 located on a proximal end of the holder protrusion 205, such that the protrusion notch 215 locks the blade 100 to the blade holder 200. As the holder protrusion 205 engages the blade aperture 120, the blade 100 preferably snaps into the protrusion notch 215, thereby preventing the blade 100 from accidentally disengaging with the blade holder 200.

The blade holder 200 further comprises, at a proximal end 207, a holder knob 220 extending from the front face 210 of the blade holder 200. The surface of holder knob 220 can include a number of ridges 222 for increased traction when in contact with a finger during use of the safety scalpel 10. As described more fully below, the holder knob 220 is adapted to move the blade 100 between the closed and open positions when in communication with the blade guard 300.

The rear face 225 (see FIG. 2D) of the blade holder 200 can include a track 240 for receiving the scalpel handle 500, preferably the blade receiving portion 550 of the scalpel handle 500. The track 240 defines lateral movement of the blade cartridge 400 when secured to the scalpel handle 500.

As illustrated in FIGS. 3A-3E and 4, the blade guard 300 is designed to slideably receive the blade 100 and blade holder 200. When the blade 100 is in the closed position, the blade guard, or blade sheath, 300 adequately surrounds the blade 100, so that the blade 100 cannot inadvertently cut, puncture, or otherwise damage materials or individuals.

Figure 3A:
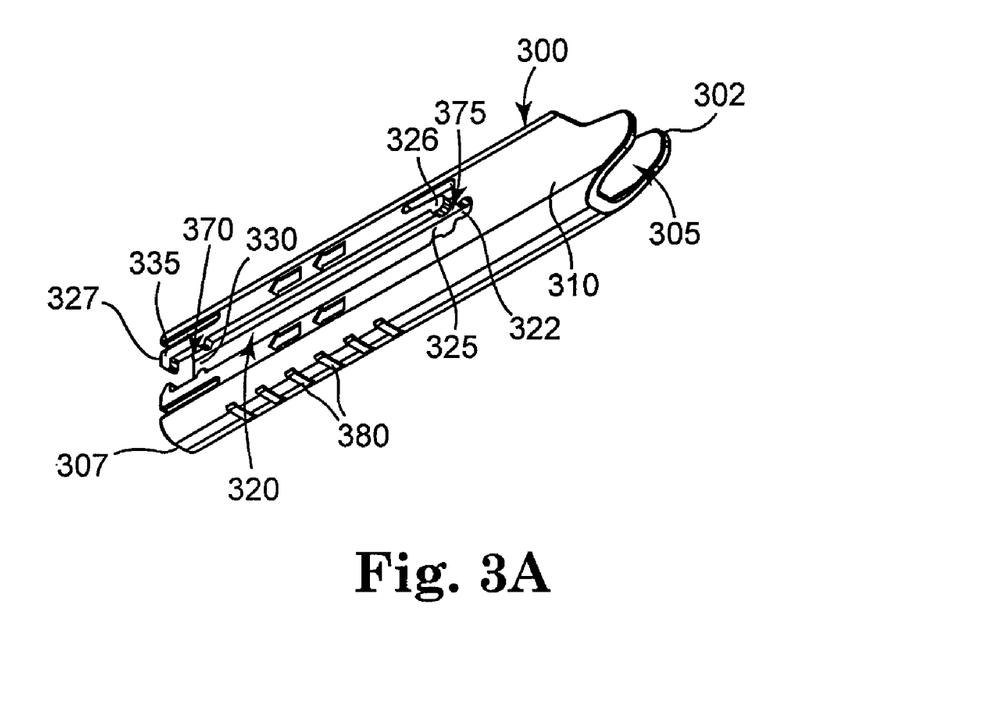
FIG. 3A illustrates a perspective view of a front face of a blade guard in accordance with a preferred embodiment of the present invention.
Figure 3B:
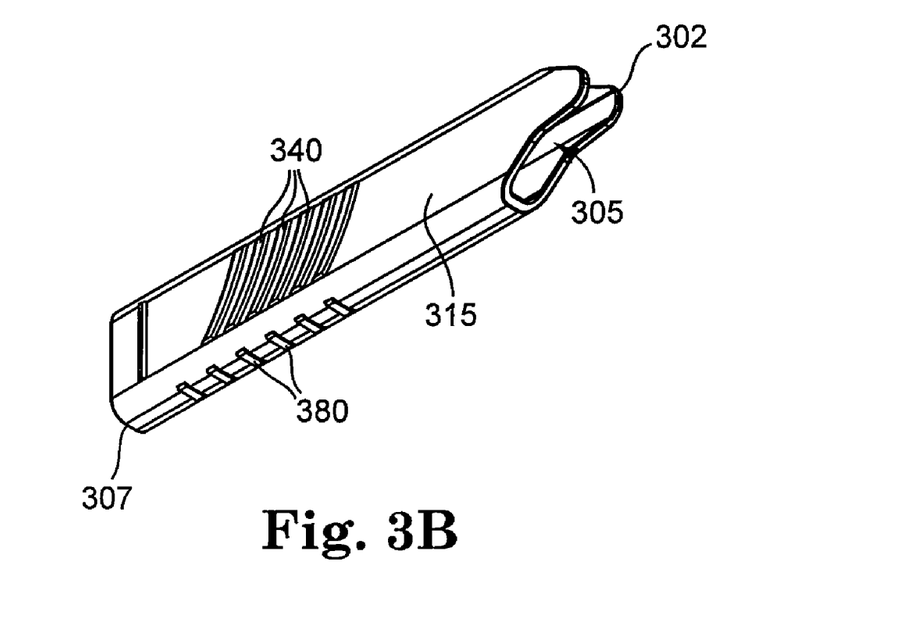
FIG. 3B illustrates a perspective view of a back face of the blade guard of FIG. 3A.
Figure 3C:
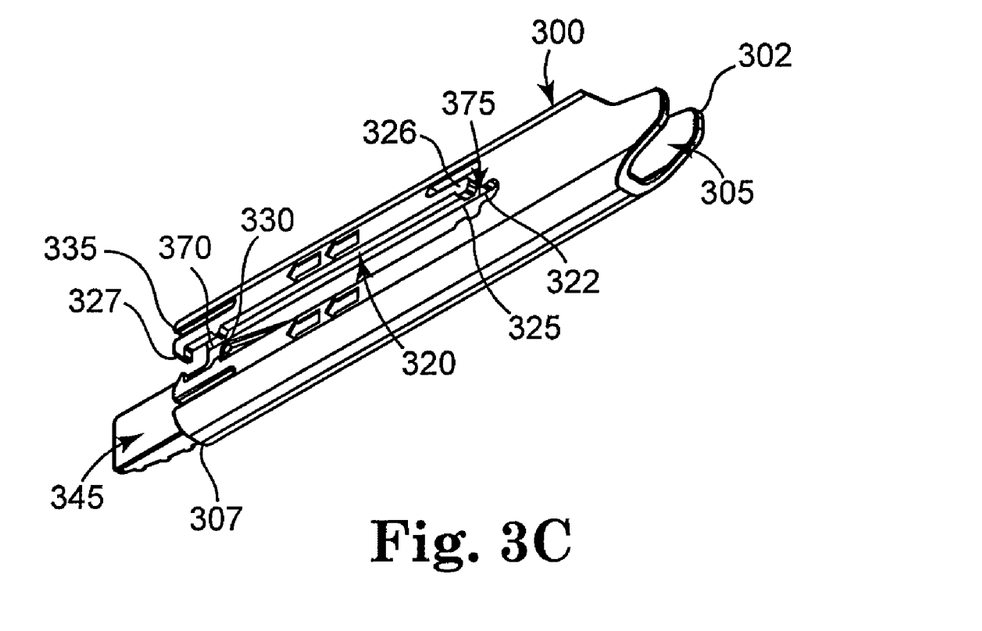
FIG. 3C illustrates a perspective view of a front face of a blade guard in accordance with another preferred embodiment of the present invention.
Figure 3D:
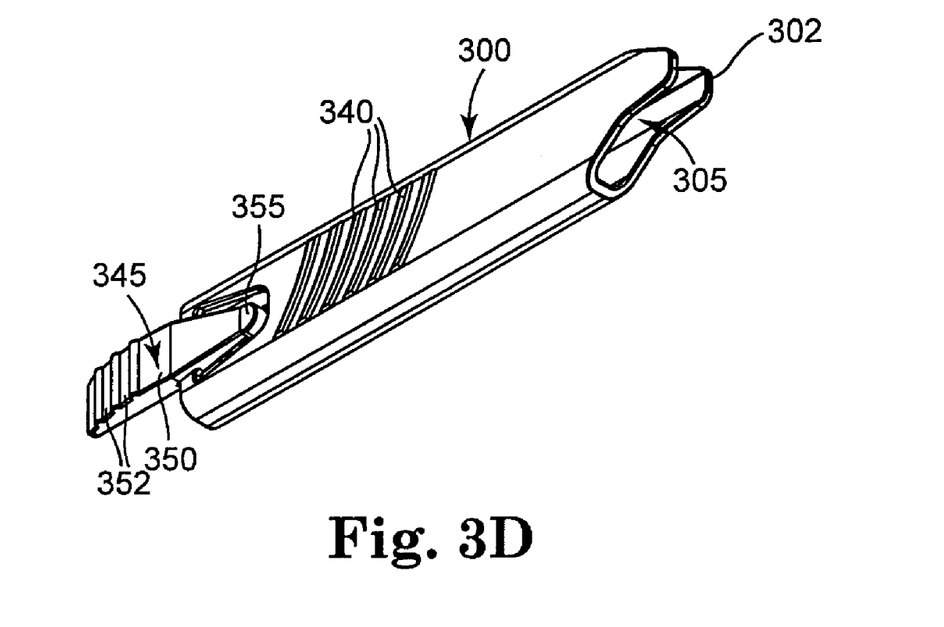
FIG. 3D illustrates a perspective view of a back face of the blade guard of FIG. 3C.
Figure 3E:
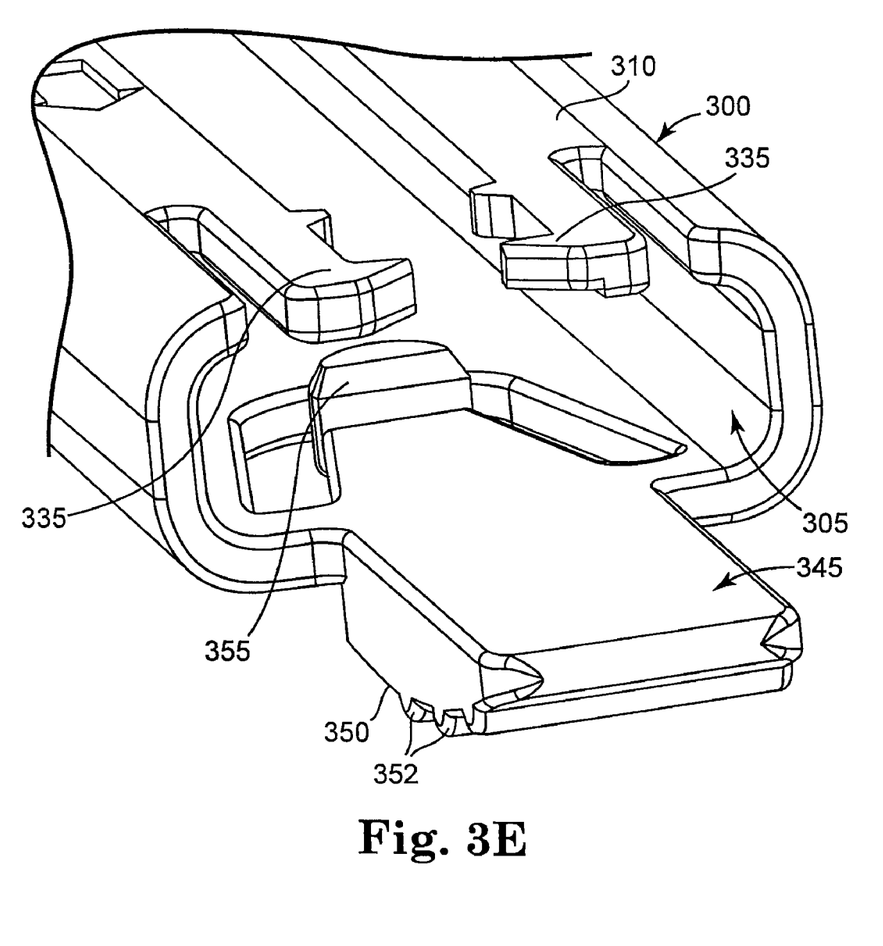
FIG. 3E illustrates a perspective view from a proximal end of the blade guard of FIG. 3C.

There are at least two preferred embodiments of the blade guard 300. A first embodiment is illustrated in FIGS. 3A-3B, while a second embodiment is illustrated in FIGS. 3C-3E. The embodiment selected can depend on the type of scalpel handle 500 used.

The blade guard 300 comprises an aperture 320 (also referred to herein as slot 320) for providing a track for the holder knob 220 of the blade holder 200 to slide between the closed and open positions. Consequently, as the holder knob 220 moves between retracted and forward positions, the blade 100 moves between the closed and open positions, respectively. More particularly, a directional force applied to the holder knob 220 of the blade holder 200 permits the holder knob 220 to slide along the slot 320 when moving the blade 100 and blade holder 200 between the closed and open positions.

The blade guard 300 defines therein a cavity 305. The blade 100 and blade holder 200 are positioned within the cavity 305 for sliding, when the holder knob 220 slides within the slot 320. The holder knob 220 is positioned near a proximal end 327 of the slot 320 when the blade 100 is in the closed position and the holder knob 220 is positioned near a distal end 322 of the slot 320 when the blade 100 is in the open position.

The blade guard 300 comprises a forward catch 325 and rear catch 330, such that the forward catch 325 is positioned near the distal end 322 of the slot 320 and the rear catch 330 is positioned near the proximal end 327 of the slot 320. The forward catch 325 is adapted to engage the holder knob 220 when the blade 100 is in the open position. The forward catch 325 prevents the blade holder 200 from moving the blade 100 forwardly beyond the open position. The forward catch 325 can include a flexible locking member 326 that locks the blade holder 200, so as to prevent unmistaken unlocking of the blade 100 in the open position. Similarly, the rear catch 330 is adapted to engage the holder knob 220 when the blade 100 is in the closed position. The rear catch 330 can prevent the blade holder 200 from moving the blade 100 rearwardly beyond the closed position. Alternatively, the rear catch 330 prevents the blade holder 200 from moving the blade 100 rearwardly beyond the fully locked position. Further, the rear catch 330 can prevent accidental unlocking of the blade holder 200, in an attempt to prevent accidents.

The blade guard 300 can include a plurality of grooves 340 positioned on the rear face 315 of the blade guard 300, as illustrated in FIGS. 3B and 3D. The plurality of grooves 340 can prevent slippage of the safety scalpel 10 during use.

The blade guard has a front face 310, as shown in FIGS. 3A and 3C, and a back/rear face 315 as shown in FIGS. 3B, 3D, and 3E. The front faces 310 of the two embodiments are preferably the same. The rear face 315, however, can have different attributes.

A beneficial feature of the differing rear faces 315 includes a method of releasing the blade guard 300, and consequently the blade cartridge 400 from the scalpel handle 500.

The blade guard 300 of FIGS. 3C and 3D further includes a latching assembly 345 for releasing the blade guard 300 from the scalpel handle 500. The latching assembly 345 includes a knob 350 extending from the rear face 315 of the blade guard 300, and a locking mechanism 355. The surface of knob 350 can include ridges 352 for increased traction when in contact with a finger during removal of the blade guard from the scalpel handle 500. As described more fully below, the knob 350 is adapted to remove the blade cartridge 400 from the scalpel handle 500.

One skilled in the art will recognize that the blade holder 200 and blade guard 300 can be made of a variety of materials including, but not limited to, plastic, such as acrylonitrile-butadiene-styrene (ABS) copolymer plastic.

As described above, the blade 100 and blade holder 200 fit into the blade guard 300. Collectively, these three elements form the blade cartridge 400. The blade cartridge 400 is attachable to and detachable from a distal end of the scalpel handle 500.

Figure 1A:
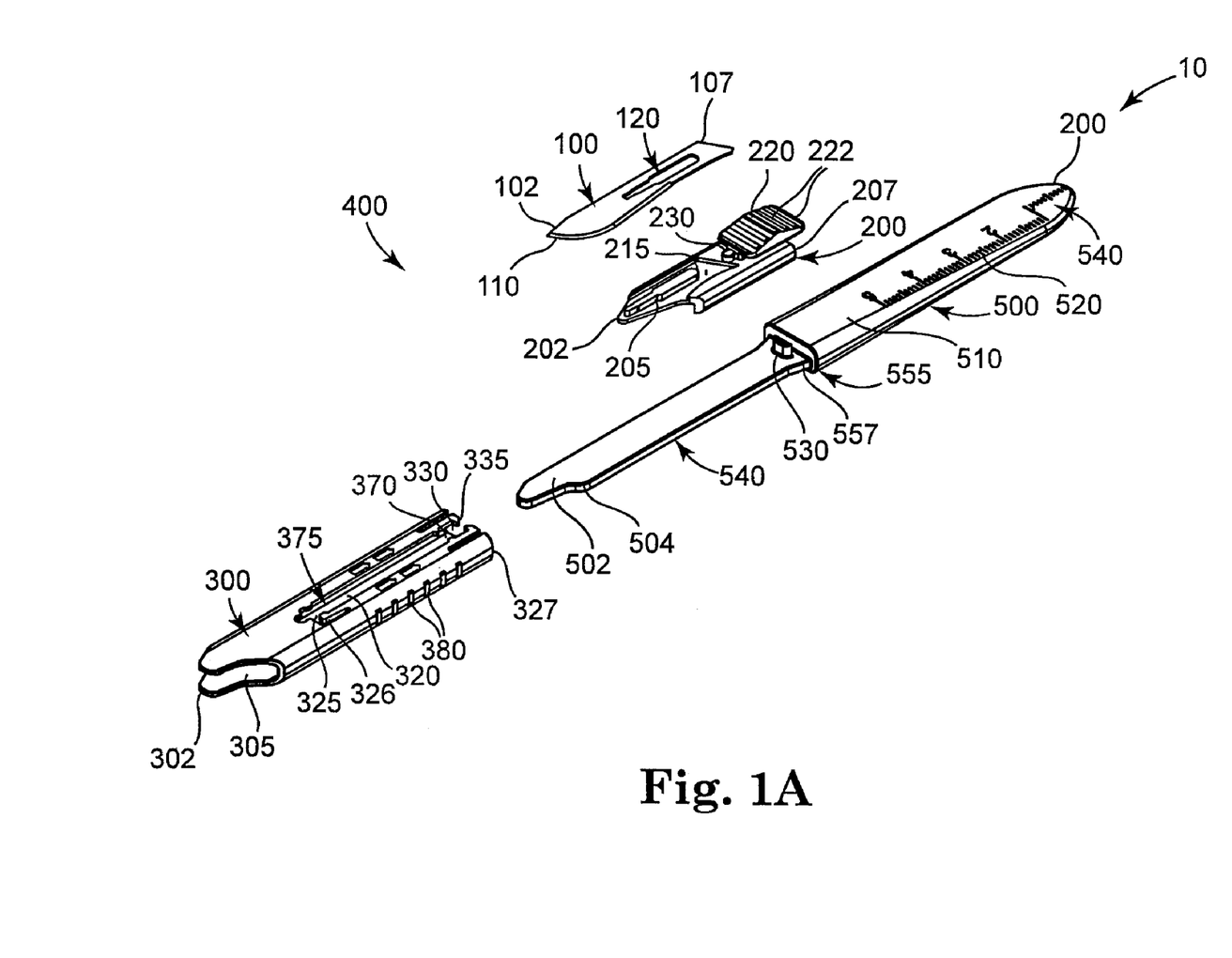
FIG. 1A illustrates a perspective view of a safety scalpel in accordance with a preferred embodiment of the present invention.
Figure 1B:
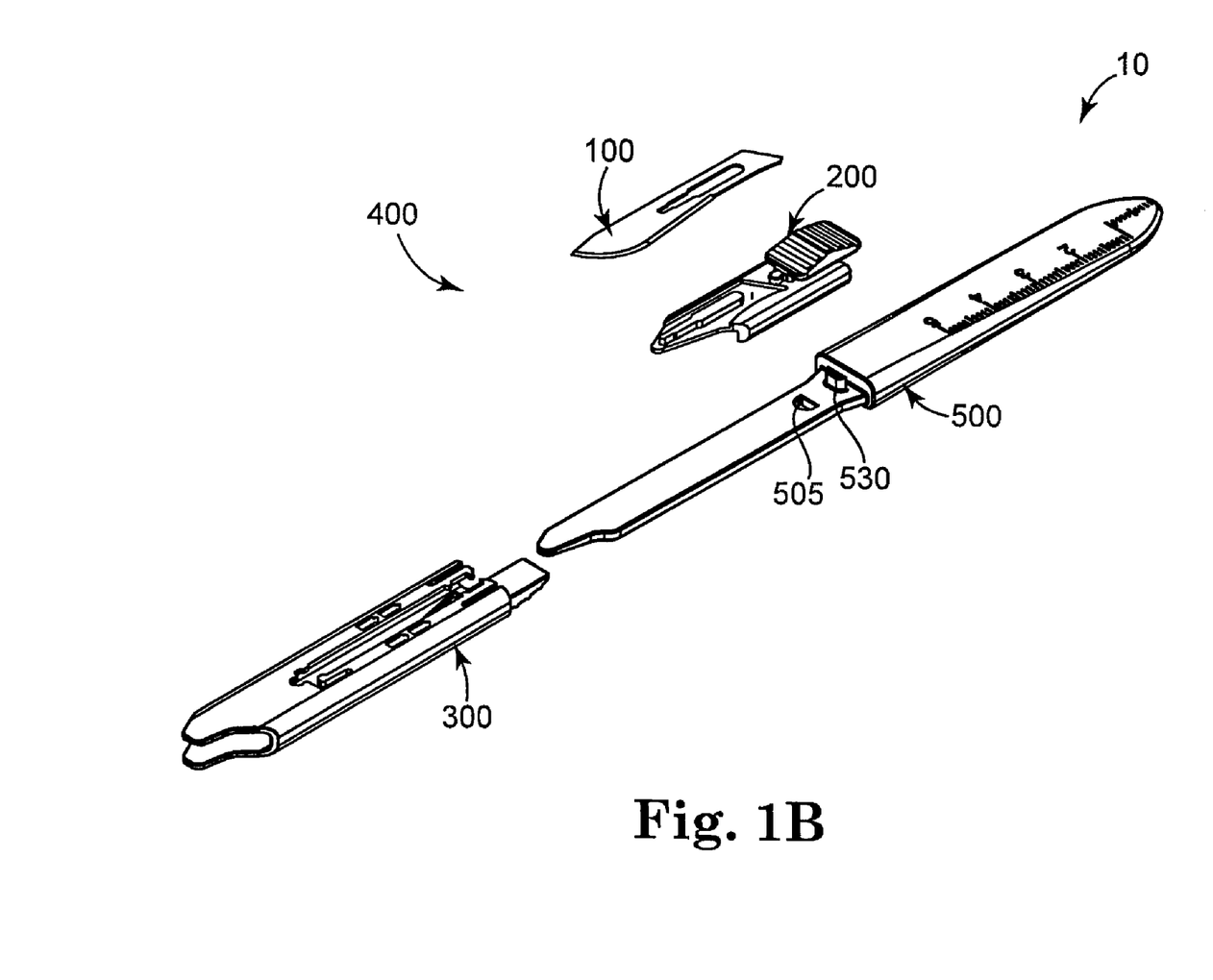
FIG. 1B illustrates a perspective view of a safety scalpel in accordance with another preferred embodiment of the present invention.

The scalpel handle 500, as shown in FIGS. 1A and 1B, comprises a handle portion 540 and a blade receiving portion 550. The handle portion 540 extends from an approximate midpoint 555 of the scalpel handle 500 to the proximal end 507 of the scalpel handle 500, while the blade receiving portion 550 extends from the approximate midpoint 555 to the distal end 502 of the scalpel handle 500.

The distal end 502 of the scalpel handle 500 can be cut on the front face 510 to accommodate the blade cartridge 400. Preferably, the distal end 502 of the scalpel handle 500 can have a tapered portion 504 for improved assembly of the safety scalpel 10.

The scalpel handle 500 comprises at least one extending member 530 on the front face 510 of the proximal end 557 of the blade receiving portion 550, such as near the approximate midpoint 555. The extending member 530 extends outwardly from the scalpel handle 500 and is adapted to enable the securing of the blade cartridge 400 to the scalpel handle 500. That is, the at least one extending member, or medial notch, 530 is adapted to engage at least one catch 335 of the blade cartridge 400 (e.g., catch 335 of the blade guard 300). When the blade cartridge 400 is attached to the scalpel handle 500, the catch 335 of the blade cartridge 400 can engage, or snap about, the extending member 530 to prevent longitudinal movement of the blade cartridge 400. In addition, lateral movement of the blade cartridge 400 is limited due to the form fitting blade receiving portion 550.

Figure 6A:
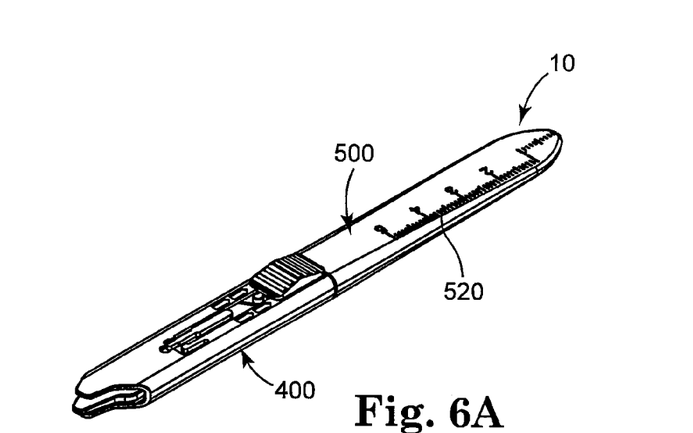
FIG. 6A illustrates a perspective view of a front face of a safety scalpel with the blade housed in the blade cartridge, in accordance with a preferred embodiment of the present invention.
Figure 6B:
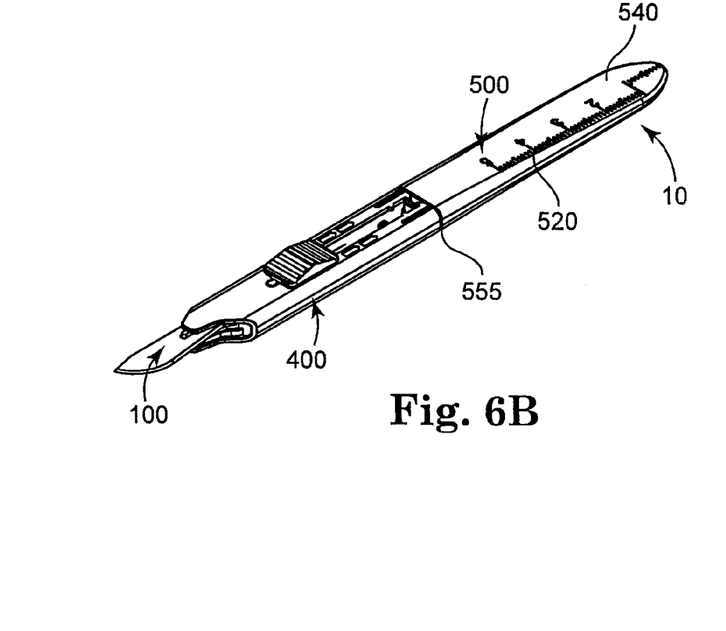
FIG. 6B illustrates a perspective view of the front face of the safety scalpel of FIG. 6A with the blade extending from the blade cartridge, in accordance with a preferred embodiment of the present invention.
Figure 6C:
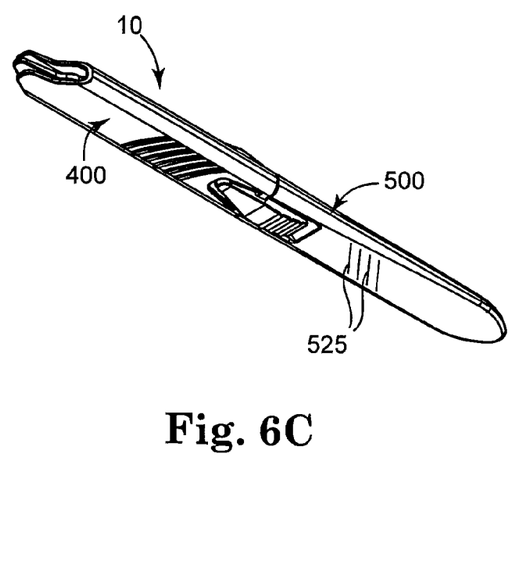
FIG. 6C illustrates a perspective view of a back face of the safety scalpel of FIG. 6A with the blade housed in the blade cartridge, in accordance with a preferred embodiment of the present invention.
Figure 7:
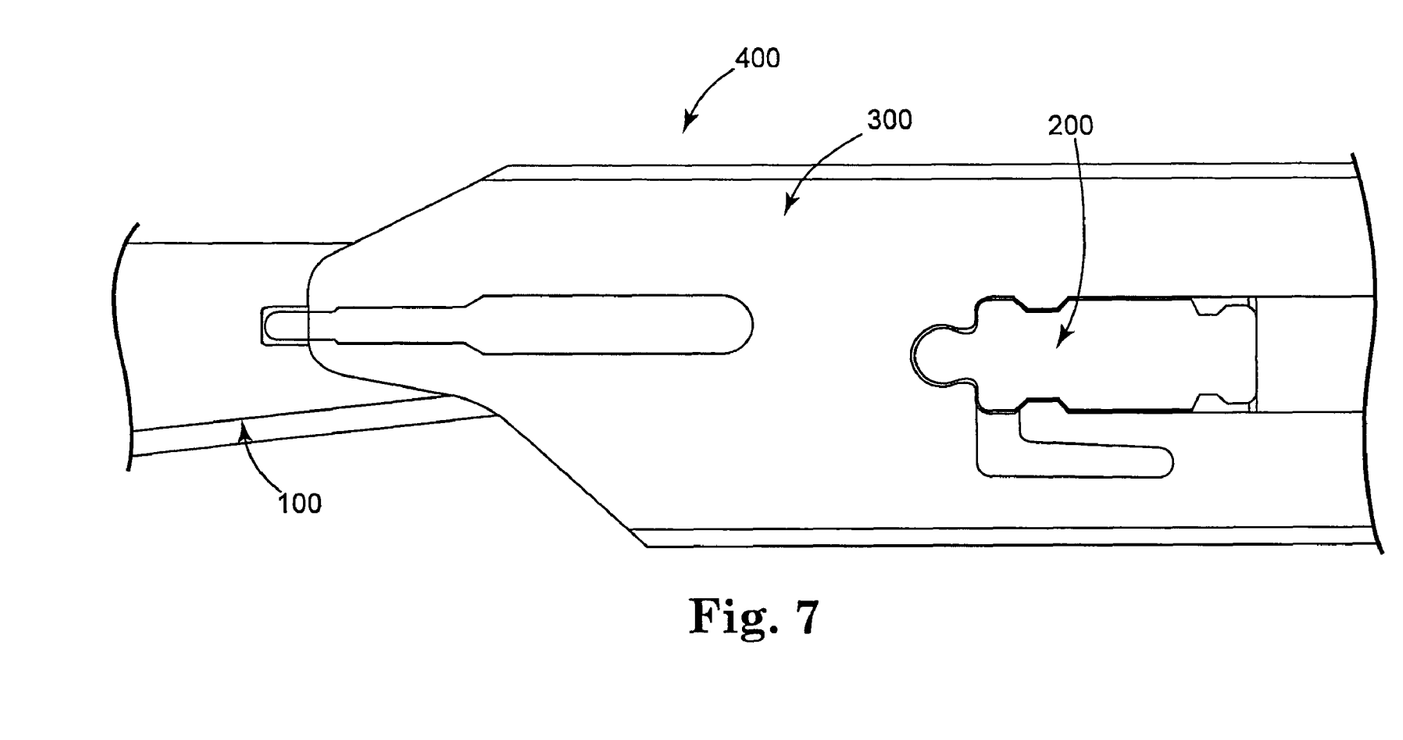
FIG. 7 illustrates a close-up, front face view of a distal end of a blade cartridge with a blade extending from a blade guard, in accordance with a preferred embodiment of the present invention.

For increased traction of the scalpel handle 500 when in contact with a finger during use of the safety scalpel 10, the handle portion 550 can include a plurality of grooves 525 positioned on a back face 515 of the scalpel handle 500, as illustrated in FIG. 6C. The plurality of grooves 525 can prevent slippage of the safety scalpel 10 during use.

As illustrated in FIGS. 1A, 1B, 6A, and 6B, the handle portion 550 of the scalpel handle 500 can include indicia 520. The indicia 520 is generally located on the front face 510 and near the proximal end 507 of the scalpel handle 500. While one skilled in the art will recognize that the indicia 520 of the present invention can include multiple markings or printings, the indicia 520 are preferably units of measurement such as, but not limited to, the metric system, the Imperial system, or many other appropriate measuring systems.

The scalpel handle 500 is designed to accept the blade cartridge 400, and provide the user with the feel of a conventional scalpel when used. It is thus provided of materials, weight, and design for comfortable use by the user.

Assembly of Blade Cartridge 400

Figure 4:
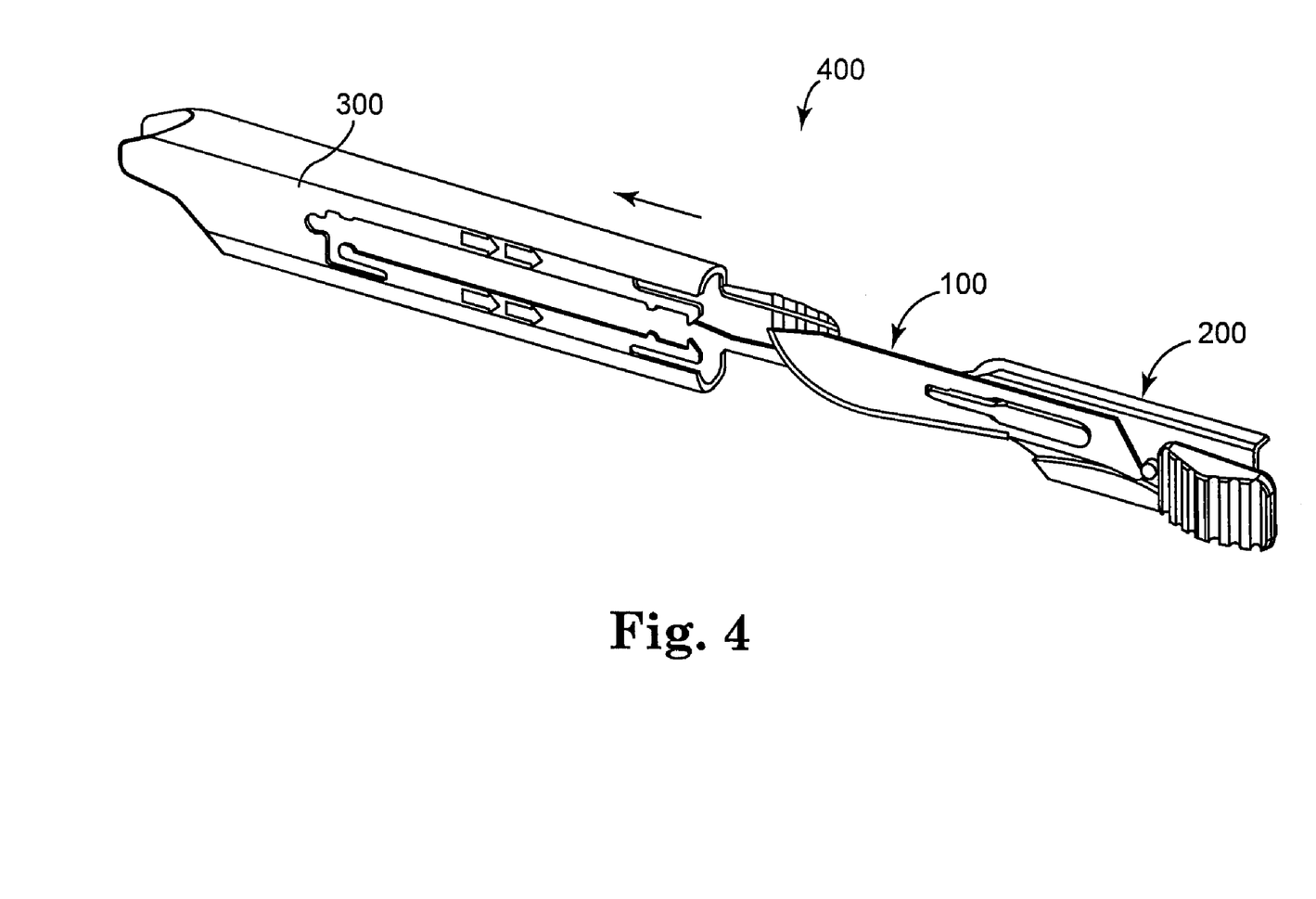
FIG. 4 illustrates a perspective view of assembly of a blade cartridge in accordance with a preferred embodiment of the present invention.

The blade cartridge 400 includes the fitted cooperation of the blade 100, the blade holder 200 and the blade guard 300, as shown in FIG. 4. Preferably, the blade cartridge 400 is assembled offsite from where the present safety scalpel 10 is ultimately used, for example, in a factory, such that only the assembled blade cartridge 400 is delivered to the user. Also, the blade 100 can be attached to the blade holder 200 through insert molding, wherein the blade holder 200 is actually formed and molded around the blade 100. With the use of insert molding, the blade 100 need not be subsequently attached to the blade holder 200.

The blade cartridge 400 can be delivered in its own sterilized wrapping such as, for example, a foil wrap. Thus, the blade cartridge 400 is not intended for the user to assemble, but is intended only for the mating of the blade cartridge 400 with the scalpel handle 500.

As described above, the blade 100 is fixed to the blade holder 200 by aligning the blade aperture 120 with the corresponding holder protrusion 205 of the blade holder 200. The protrusion notch 215 permits the blade 100 to be secured onto the blade holder 200, as shown in FIGS. 2A and 2B.

The blade holder 200 with the blade 100 is then attached to the blade guard 300 by sliding and slotting the blade holder 200 into the aperture 305 of the blade guard 300. This is shown by the arrow in FIG. 4.

To attach the blade 100 and blade holder 200 into the blade guard 300, the blade 100 and blade holder 200 are inserted into the blade guard 300, such that the blade 100 is aligned within the cavity 305 defined by the lateral sides of the blade guard 300 and the holder knob 220 fits into slot 320. As illustrated in FIG. 4 (see arrow), the blade holder 200 is slotted into the blade guard 300 such that the stopper rib 230 on the blade holder 200 engages the rear retaining slot 370 of the blade guard 300.

The blade holder 200 and the blade 100 are kept temporarily locked in the blade guard 300 by the holder stopper rib 230 engaging and locking to the matching rear retaining slot 370 on the blade guard 300. Accordingly, the blade 100 can be kept in the closed position.

In the assembled blade cartridge 400, the blade 100 is wholly enclosed in the blade guard 300 until mounted on the scalpel handle 500 for use.

Mounting of Blade Cartridge 400 to Scalpel Handle 500

As shown in FIGS. 1A and 1B, the process of mounting the assembled blade cartridge 400 to the scalpel handle 500 is fairly simple. The distal end 502 of the scalpel handle 500, i.e., the blade receiving portion 550, can be inserted into the cavity 305 of the blade cartridge 400, preferably at the proximal end 307. Indeed, the blade receiving portion 550 of the scalpel handle 500 can be housed in the track 240 of the rear face 225 of the blade holder 200 to secure the blade cartridge 400 to the scalpel handle 500. The blade cartridge 400 slides to the point where the catch 335 engages an extending member 530.

Figure 5:
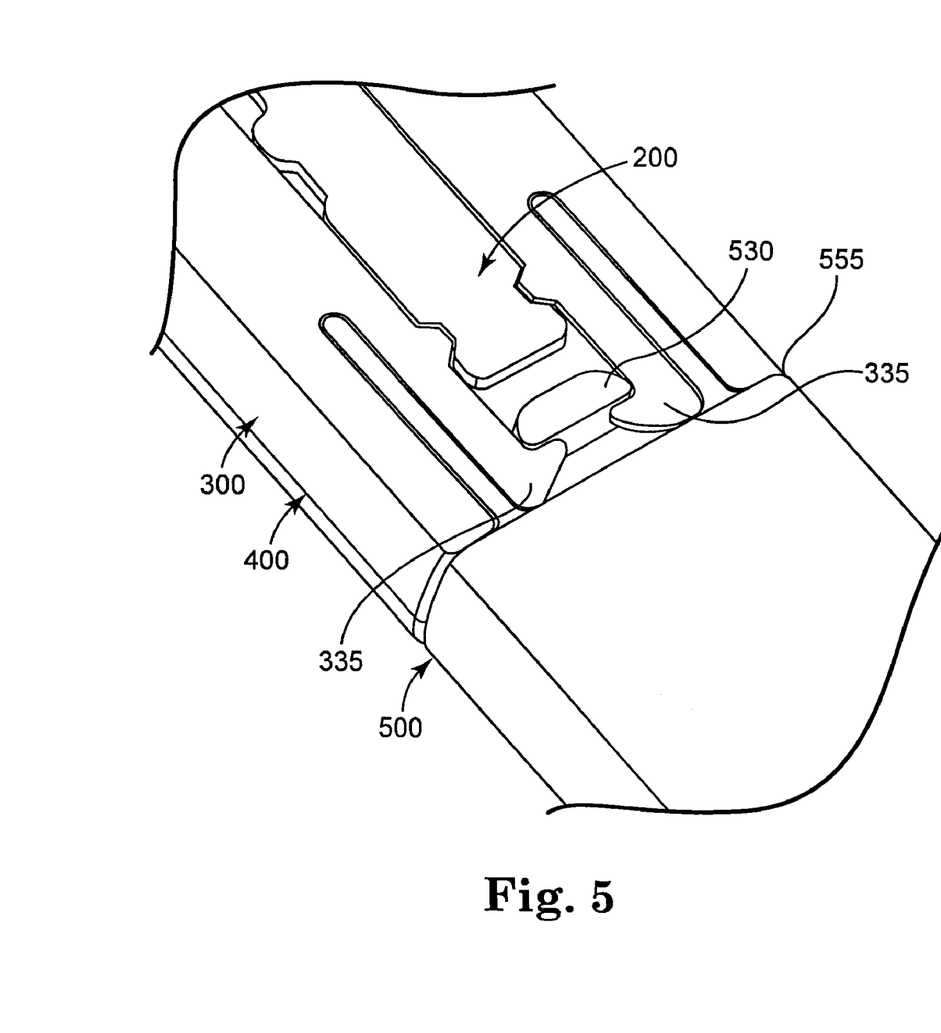
FIG. 5 illustrates a front face, perspective view of the blade cartridge attached to a scalpel handle.

The catch 335 of the blade cartridge 400 is arranged to latch around the extending member 530. Further, the proximal end 307 of the blade cartridge 400 (e.g., proximal end 307 of the blade guard 300) is adapted to abut against the approximate midpoint 555 of the scalpel handle 500, such that the blade cartridge 400 has limited, or no, longitudinal and/or lateral movement. FIG. 5 illustrates a close up of the blade cartridge 400 secured to the scalpel handle 500, such that the catch 335 is latched to the extending member 530.

In addition, when the scalpel handle 500 includes an aperture 505, the blade cartridge 400 can be further secured to the scalpel handle 500. The blade cartridge 400 (e.g., the blade guard 300) can include the latching assembly 345. The latching assembly 345 includes a locking mechanism 355 that engages the aperture 505 of the rear face the scalpel handle 500. This engagement further secures the blade cartridge 400 to the scalpel handle 500.

Use of Safety Scalpel 10

When first mounted, the blade 100 in the blade cartridge 400 is in the closed position, as illustrated in FIGS. 6A and 6C. The blade 100 can be extended out of the blade guard 300 by depressing the holder knob 220 of the blade holder 200 (e.g., pushing the holder knob 220 downward) or alternatively simply pushing outward towards the distal end 202 of the blade holder 200; releasing the stopper rib 230 on the blade holder 200 from the rear retaining slot 370 on the blade guard 300; sliding the holder knob 220 along the slot 320 of the blade guard 300 until the blade 100 reaches the open position, upon which the holder knob 220 is released such that the stopper rib 230 on the blade holder 200 engages the front retaining slot 375 on the blade guard 300. Thus, the blade 100 is temporarily locked in the open position. When the blade guard 300 engages the front retaining slot 375, the flexible locking member 326 can be moved outwardly toward an edge of the blade guard 300, such that it locked.

In this open position, as shown in FIG. 6B, the safety scalpel 10 is ready for use, i.e., cutting and/or slicing. Further, in this position, the blade 100 is prevented from moving laterally and transversally during use of the safety scalpel 10.

The blade cartridge 400 (e.g., the blade guard 300) can further comprise a plurality of indentations 380, as illustrated in FIGS. 1A, 3A, and 3B. The plurality of indentations 380 are positioned on at least one lateral side/edge of the blade guard 300, such that the plurality of indentations 380 provide increased grip of the safety scalpel 10 during use.

If the user needs to hand the safety scalpel 10 to a colleague, she first moves the blade 100 into the closed position by depressing the holder knob 220 on the blade holder 200 to release the stopper rib 230 from the front retaining slot 375. Alternatively, she can move the holder knob 220 towards the proximal end 307 of the blade guard 300. In either case, this causes a sliding of the holder knob 220 back along the slot 320 of the blade guard 300, until the blade 100 reaches the closed position, upon which the holder knob 220 is released such that the stopper rib 230 on the blade holder 200 re-engages the rear retaining slot 370 on the blade guard 300. The blade 100 is now temporarily locked in the closed position. The blade 100 can be moved any number of times between the open and closed positions until the operation is completed.

Dismounting of Blade Cartridge 400 from Scalpel Handle 500

Because there are at least two embodiments of the scalpel handle 500 that can use two different blade guards 300, there are two different processes of dismounting the blade cartridge 400 (e.g., blade guard 300) from the safety handle 500.

In a first embodiment, the blade guard 300 of FIGS. 3A and 3B is secured to the scalpel handle 500 of FIG. 1A. That is, there is no aperture 505 (see FIG. 1B).

The blade guard 300 in this first embodiment is removed by having the holder knob 220 placed in the rear retaining slot 370, such that the blade 100 is in the closed position and does not extend from the blade guard 300. The holder knob 220 can be slid slightly further towards the proximal end 307 of the blade cartridge 400 (e.g., proximal end 307 of the blade guard 300), or towards the approximate midpoint 555. When the holder knob 220 slides in this direction, the catch 335 moves away from the extending member 530 of the scalpel handle 500. This can release the blade cartridge 400 from the scalpel handle 500. Then, the user need only slide the entire blade cartridge 400 towards the distal end 502 of the scalpel handle 500, or off the scalpel handle 500.

In a second embodiment, the scalpel handle 500 includes an aperture 505 in proximity to the extending member 530, preferably slightly offset towards the distal end 502. In this embodiment, the blade cartridge 400 (e.g., the blade guard 300) further includes the locking mechanism 355 about its rear face 315.

Once the locking mechanism 355 is removed from the aperture 505, the catch 335 can be released from the extending member 530, as described above. Then, the blade cartridge 400 is loose enough to be released from the scalpel handle 500. In essence, the latching assembly 345 is an additional safety feature to help ensure the blade cartridge 400 does not mistakenly release from the scalpel handle.

The rear face 315 of the blade cartridge 400 (e.g., the rear face 315 of the blade guard 300) matches up with the rear face 515 of the scalpel handle 500. When the blade cartridge 400 is secured to the scalpel handle 500, the latching assembly 345 is adapted to engage the aperture 505 of the scalpel handle 500. The latching assembly 345 includes the knob 350 and the locking mechanism 355. Because the locking mechanism is an inwardly extending mechanism, it engages the aperture 505 in its normal state. If the knob 350 is depressed, however, the locking mechanism 355 disengages from the aperture 505. The knob 350 can include a plurality of ridges for increased traction in disengaging the locking mechanism 355 from the aperture 505.

Disposable Safety Scalpel 10

In another alternative embodiment of the present invention, the safety scalpel 10 comprises a disposable scalpel handle 500, such that the disposable scalpel handle 500 is separate and passive from the blade cartridge 400. The disposable scalpel handle 500 is adapted to attach to the blade cartridge 400. Preferably, the blade cartridge 400 and the disposable scalpel handle 500 are permanently fixed to each other at the factory during the manufacturing process of the safety scalpel 10. After use, the blade cartridge 400 and disposable scalpel handle 500 can be properly discarded.

One skilled in the art will recognize that the disposable scalpel handle 500 can be made of a variety of materials including, but not limited to, plastic, such as acrylonitrile-butadiene-styrene (ABS) copolymer plastic.

In yet another alternative embodiment of the present invention, the safety scalpel 10 comprises a disposable scalpel handle 500 having a slideable blade 100 and blade holder 200 received therein. Accordingly, the blade guard 300 is an integral part of the disposable scalpel handle 500 and, therefore, does not detach from the scalpel handle 500. Further, the entire safety scalpel 10 is disposable after use.

The blade cartridge 400 and scalpel handle 500 can be attached and detached as described above.

One skilled in the art will recognize that the scalpel handle 500 (e.g., the entire safety scalpel 10, minus the blade 100) can be made of a variety of materials including, but not limited to, plastic, such as acrylonitrile-butadiene-styrene (ABS) copolymer plastic.

While the invention has been disclosed in its preferred forms, it will be apparent to those skilled in the art that many modifications, additions, and deletions can be made therein without departing from the spirit and scope of the invention and its equivalents, as set forth in the following claims.

We claim:

1. A safety scalpel comprising:
a three component blade cartridge comprising:
a blade;
a blade holder in communication with the blade wherein the blade holder comprises a holder knob; and
a blade guard adapted to receive the blade and blade holder, comprising a slot for the holder knob to slide within, the holder knob positioned near a proximal end of the slot when the blade is in a closed position relative to the blade guard, and the holder knob positioned near a distal end when the blade is in an open position relative to the blade guard; and
a scalpel handle comprising a handle portion extending from an approximate midpoint to a proximate end of the scalpel handle and a blade receiving portion extending from the approximate midpoint to a distal end of the scalpel handle, said handle portion and said blade receiving portion have lengths extending in a first direction,
wherein the blade cartridge is releasably attached to the blade receiving portion so that the blade cartridge can be easily removed and replaced by a user,
further wherein the blade cartridge comprises linear guides, enabling the blade cartridge to slide linearly along the linear guides onto the blade receiving portion of the scalpel handle when a length of said blade cartridge is parallel to said first direction,
and the blade holder of the blade cartridge is in slidable contact with the blade receiving portion of the scalpel handle, the blade cartridge lockable to the scalpel handle.

2. The safety scalpel of claim 1, wherein the scalpel handle includes an extending member, wherein the blade cartridge includes a catch for engaging the extending member, and wherein the catch engaging the extending member locks the blade cartridge to the scalpel handle.

3. The safety scalpel of claim 1, wherein the blade is not exposed beyond the blade cartridge when in the closed position, and wherein the blade is exposed beyond the blade cartridge when in the open position.

4. The safety scalpel of claim 1, wherein the scalpel handle includes an extending member, wherein the blade cartridge includes a catch for engaging the extending member, wherein the catch engaging the extending member locks the blade cartridge to the scalpel handle, and wherein the holder knob enables the blade to move from a closed position, wherein the blade is not exposed beyond the blade cartridge, to an open position, wherein the blade is exposed beyond the blade cartridge.

5. The safety scalpel of claim 1, the blade holder comprising a front face in communication with the blade, and a substantially flat, back face.

6. The safety scalpel of claim 5, the blade holder further comprising a holder protrusion extending from the front face, the holder protrusion having a profile that corresponds to an aperture of the blade for securedly engaging the aperture of the blade.

7. The safety scalpel of claim 5, the blade holder further comprising a pair of tracks extending from the substantially flat, back face.

8. The safety scalpel of claim 7, wherein when the blade cartridge is secured to the scalpel handle, the back face of the blade holder slides along a first face of the blade receiving portion of the scalpel handle and the pair of tracks engage sides of the blade receiving portion of the scalpel handle.

9. The safety scalpel of claim 7, the pair of tracks of the blade holder engaging sides of the blade receiving portion of the scalpel handle to enable sliding of the blade holder in contact with the blade receiving portion of the scalpel handle.

10. The safety scalpel of claim 1, the blade holder carrying the blade and the holder knob extending from a front face.

11. A safety scalpel comprising:
a three component blade cartridge assembly comprising:
a blade comprising a cutting edge at a distal end and defining an aperture at a proximal end;
a blade holder comprising a holder knob and a front face with an extending member configured to cooperatively engage the aperture of the blade for carrying the blade, and a rear face being substantially flat; and
a blade guard defining a cavity configured to receive the blade holder and the blade therein, and a slot for the holder knob to slide within, the holder knob positioned near a proximal end of the slot when the blade is in a closed position relative to the blade guard, and the holder knob positioned near a distal end when the blade is in an open position relative to the blade guard; and
a scalpel handle comprising an elongated body comprising:
a handle portion extending from an approximate midpoint to a proximate end of the scalpel handle; and
a blade receiving portion extending from the approximate midpoint to a distal end of the scalpel handle, said handle portion and said blade receiving portion have lengths extending in a first direction;
wherein the blade cartridge is releasably attached to the blade receiving portion so that the blade cartridge can be easily removed and replaced by a user;
further wherein the blade cartridge comprises linear guides enabling the blade cartridge to slide linearly along the linear guides onto the blade receiving portion of the scalpel handle when a length of said blade cartridge is parallel to said first direction,
wherein the rear face of the blade holder is in slidable contact with the blade receiving portion of the scalpel handle, and
wherein the blade guard is lockable to the blade receiving portion of the scalpel handle.

12. The safety scalpel of claim 11, the blade holder further comprising a pair of tracks extending from the rear face away from the front face, the pair of tracks configured to cooperatively engage opposing sides of the blade receiving portion of the scalpel handle.

13. The safety scalpel of claim 11, wherein the slot having a first catch for maintaining the blade in the closed position and a second catch for maintaining the blade in the open position.

14. The safety scalpel of claim 11,
the blade receiving portion of the scalpel handle comprising an extending member,
the blade cartridge comprising a catch for engaging the extending member, and
the extending member locks the blade cartridge to the scalpel handle when engaged by the catch.

* * * * *